US008809765B2

(12) United States Patent
Weisshaar et al.

(10) Patent No.: US 8,809,765 B2
(45) Date of Patent: Aug. 19, 2014

(54) SENSOR PROTECTOR

(75) Inventors: Stefan Weisshaar, Adelebsen (DE); Michael Bates, Gloucester (GB); Christian Pradel, Kalefeld-Sebexen (DE); Volker Limpert, Morschen (DE)

(73) Assignee: Sartorius Stedim Biotech GmbH (DE)

( * ) Notice: Subject to any disclaimer, the term of this patent is extended or adjusted under 35 U.S.C. 154(b) by 83 days.

(21) Appl. No.: 13/513,344

(22) PCT Filed: Nov. 12, 2010

(86) PCT No.: PCT/EP2010/006917
§ 371 (c)(1),
(2), (4) Date: Jul. 11, 2012

(87) PCT Pub. No.: WO2011/066901
PCT Pub. Date: Jun. 9, 2011

(65) Prior Publication Data
US 2012/0267518 A1 Oct. 25, 2012

(30) Foreign Application Priority Data
Dec. 1, 2009 (DE) .................. 10 2009 056 417

(51) Int. Cl.
*G01J 1/02* (2006.01)
(52) U.S. Cl.
USPC ........................................................ 250/239
(58) Field of Classification Search
USPC .................................. 250/239, 269.3
See application file for complete search history.

(56) References Cited

U.S. PATENT DOCUMENTS

| 5,781,817 | A | 7/1998 | Nomura et al. | |
| 6,265,713 | B1 * | 7/2001 | Berard et al. | 250/269.3 |
| 6,472,660 | B1 * | 10/2002 | Hother | 250/269.1 |
| 6,653,148 | B2 | 11/2003 | Trapp et al. | |
| 6,704,385 | B1 * | 3/2004 | Reichenauer | 250/269.3 |
| 6,965,461 | B1 | 11/2005 | Chiang et al. | |
| 7,355,845 | B2 | 4/2008 | Kim et al. | |

(Continued)

FOREIGN PATENT DOCUMENTS

| CA | 2 349 850 | 5/2000 |
| DE | 197 02 495 | 7/1997 |

(Continued)

OTHER PUBLICATIONS

International Preliminary Report.

*Primary Examiner* — Seung C Sohn
(74) *Attorney, Agent, or Firm* — Gerald E. Hespos; Michael J. Porco; Matthew T. Hespos

(57) ABSTRACT

A sensor protector is intended to reduce the sensitivity of the optical sensor (4) to radiation products which, for example, are formed during sterilization with gamma radiation and to ensure simple and cost-effective manufacture. The sensor protector includes an upper part (1), a lower part (3) and an optical sensor (4). The optical sensor (4) situated on the lower part is positionable in an offset manner with respect to an opening (2) situated in the upper part and movable by means of displacement toward the opening (2) of the upper part (1). The sensor protector is suitable for use in containers and laboratory products that are sterilized by gamma radiation, for example disposable bioreactors.

16 Claims, 2 Drawing Sheets

(56) References Cited

U.S. PATENT DOCUMENTS

| | | |
|---|---|---|
| 7,390,462 B2 | 6/2008 | Rao et al. |
| 2004/0213114 A1 | 10/2004 | Oishi et al. |
| 2006/0028928 A1 | 2/2006 | Wang et al. |
| 2006/0146403 A1 | 7/2006 | McWilliams |
| 2007/0185472 A1 | 8/2007 | Baumfalk et al. |
| 2007/0289227 A1 | 12/2007 | Parker et al. |
| 2009/0075362 A1 | 3/2009 | Baumfalk et al. |

FOREIGN PATENT DOCUMENTS

| | | |
|---|---|---|
| DE | 198 51 018 | 5/2000 |
| DE | 199 44 714 | 12/2000 |
| DE | 100 51 220 | 4/2002 |
| DE | 103 26 848 | 6/2005 |
| DE | 12 2004 031 082 | 1/2006 |
| DE | 20 2007 005 399 | 8/2007 |
| DE | 10 2009 003 971 | 7/2010 |
| WO | 02/056023 | 7/2002 |

* cited by examiner

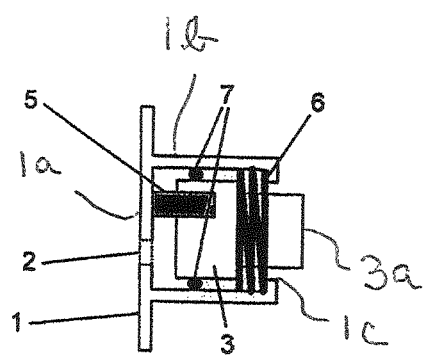
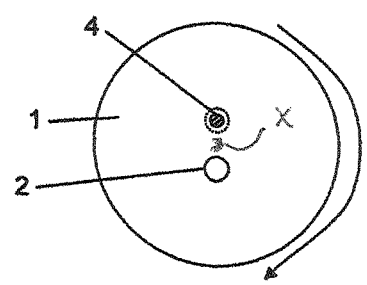
Figure 1a                    Figure 1b
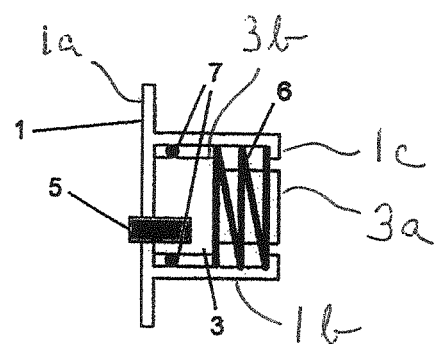
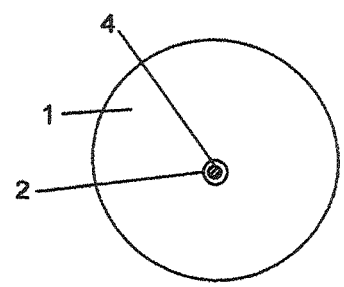
Figure 2a                    Figure 2b

SENSOR PROTECTOR

BACKGROUND OF THE INVENTION

1. Field of the Invention

The invention relates to a sensor protector for optical sensors.

2. Description of the Related Art

Optical sensors are used particularly in disposable reactors or containers, mixing reactors or containers, and bioreactors or biocontainers in medical technology and biotechnology. In these and similar application areas, it is often necessary to sterilize a container before use. In the field of disposable products, radiation, more particularly gamma radiation, has been found to be effective for sterilization, but is, however, damaging to optical sensors. This is particularly the case for optical sensors based on porous matrices, for example fluorescence-based pH sensors. Therefore, such sensors require an effective protective system which, at the same time, is cost-effectively implementable.

WO 02/056023 A1 and DE 10 051 220 A1 disclose optical sensors for measuring at least one parameter in a sample. These sensors are based on a device for exciting the fluorescence of an analyte-sensitive fluorescent dye immobilized in a matrix in a sample vessel or reactor, which dye is in at least indirect contact with the sample, and on an evaluation device for the resulting fluorescence response signal. The analyte concentration can be evaluated or determined in this case by utilizing both the fluorescence decay time and the fluorescence intensity. A disadvantage is that such pH sensor patches, based on a hydrophilic support matrix, for example impregnated papers or sol-gel matrices, are damaged in a dose-dependent manner during radiation sterilization. There is a reduction in both the intensity of the fluorescence of the dye(s), and the sensitivity of the sensor patch with respect to the measured variable.

U.S. Pat. No. 7,390,462 B2 discloses a sensor in which the fluorescent dye is present immobilized in a hydrophilic matrix. It claims a sensor having the pH-sensitive fluorescent dye MA-HPDS present in a hydrogel. In this case, too, it is a disadvantage that such hydrophilic optical sensors are damaged in a dose-dependent manner during sterilization with gamma radiation. Such radiation is used particularly in laboratory technology for containers composed of polymers. There is a reduction in both the intensity of the fluorescence of the dye(s), and the sensitivity of the sensor with respect to the measured variable. Particularly severe damage to such a sensor patch occurs when it is in contact during the radiation sterilization with a relatively large volume of air, or else with conventional protective gasses, for example nitrogen or argon. During the radiation sterilization, the gasses are partly ionized, or free radicals are generated. These radicals react, for example, during the sterilization of a gas-filled polymer bag, on the walls or else on the sensor surfaces. Sensors based on porous, hydrophilic matrices are particularly vulnerable to this, since the sensor chemistry as a matter of principle has to be present immobilized on the surface, or inner surface, of the matrix, so that the sample to be measured can come into contact with the sensor chemistry. The extent of the damage depends firstly on the irradiation dose and secondly on the ratio of surface area to volume of the irradiated container containing the sensor patch. This ratio determines the number of ions or radicals which damage the sensor patch, or the sensor chemistry contained therein.

DE 10 2009 003 971.6 discloses an optical sensor for measuring at least one parameter, which sensor is porously covered by a noble metal layer, and so reaction of reactive particles on the noble metal layer is achieved. However, a disadvantage in this case is that such a coating is technically and mechanically difficult to achieve and is associated with high costs, and this should be avoided particularly in the field of disposable products.

It is therefore an object of the present invention to develop a sensor protector for an optical sensor in which the sensitivity of the optical sensor to radiation, more particularly gamma radiation, is reduced and which is implementable in a cost-effective and simple manner.

SUMMARY OF THE INVENTION

The sensor protector according to the invention comprises an upper part and a lower part. The upper part comprises at least one opening. The lower part comprises at least one optical sensor. The optical sensor and the opening are positionable offset from one another. In the closed state, the upper part covers the sensor. Thus, said sensor is, for example, protected from mechanical influences. As a result of displacement, it is possible to move the optical sensor toward the opening, and the sensor is thus accessible to the medium.

In a particularly preferred embodiment of the invention, the lower part comprises at least one projection which contains one or more optical sensors. The projection constitutes, for example, protection for the optical sensor.

In a further preferred exemplary embodiment, the projection is smaller than the opening. Thus, in the open state, it is possible to slide the projection through the opening.

In a further particularly preferred embodiment, the surface of the lower part is flush with the surface of the optical sensor. Thus, contact between the optical sensor and reactive ions formed as a result of radiation sterilization, or other agents and substances, is minimized.

In a particularly preferred embodiment, a variable force pushes the lower part onto the upper part. This ensures that the optical sensor does not unexpectedly reach the opening. If a projection is present, the variable force pushes the lower part in the direction of the upper part, and the projection on which or in which at least one optical sensor is located onto the upper part. In the event of a displacement in the direction of the opening, a projection which is smaller than the opening is pushed through said opening and arrested. The projection is then located outside and is easily accessible to media to be measured. The variable force here can, for example, be a spring force exerted by a spring, pneumatic force or hydraulic force.

In a further preferred embodiment of the invention, the upper part is mounted rotatably with respect to the lower part. The optical sensor is displaceable toward the opening by means of rotation. In this case, a rotary joint or a ball joint is possible for example.

In a further advantageous embodiment of the invention, the upper part and the lower part are made from plastic, lowering manufacturing costs.

In a preferred embodiment of the invention, in the closed state of the protector, the optical sensor is sterilizable by radiation while maintaining its functionality. The sensor protector reduces the sensitivity to sterilization, for example by means of ionizing radiation, gamma radiation, UVC, beta or electron radiation. As a result of the minimization of the volume of gas in the immediate proximity of the optical sensor, there is a corresponding reduction in the number of reactive particles formed therefrom, which are formed as a result of radiation sterilization and which have access to the optical sensor and react with the matrix thereof and the fluorescent dye(s). Thus, a better signal-to-noise ratio, and a generally higher sensitivity of the optical sensor with respect to its measured variable, is achieved. The measured variables can in this case be, for example, pH, the dissolved oxygen concentration or other parameters. After radiation sterilization or before use of the container, for example as bioreactor, the sensor protector is openable without breaking the sterile barrier of the container.

In a particularly preferred embodiment of the invention, the sensor protector is used in chemical or biological equipment, for example in a bioreactor. In this case, it is used for determining at least one parameter, for example pH or dissolved oxygen concentration.

BRIEF DESCRIPTION OF THE DRAWINGS

FIG. 1a shows a diagrammatic cross section through an exemplary embodiment of the sensor protector in the closed state, wherein a spring presses the optical sensor onto the upper part.

FIG. 1b shows a top view of an exemplary embodiment of the sensor protector according to FIG. 1a.

FIG. 2a shows a diagrammatic cross section through an exemplary embodiment of the sensor protector in the open state.

FIG. 2b shows a top view of an exemplary embodiment of the sensor protector according to FIG. 2a.

DETAILED DESCRIPTION OF THE PREFERRED EMBODIMENTS

Figure 3:
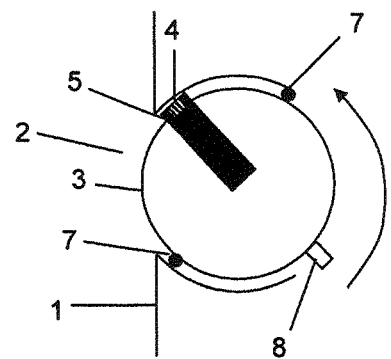
FIG. 3 shows a diagrammatic cross section through an exemplary embodiment of the sensor protector in the closed state.

According to FIGS. 1a to 4, the sensor protector has an upper part 1 and a lower part 3. The lower part 3 has a sensor housing 3a and an optical sensor 4 is mounted in or on a projection 5 that is connected to the sensor housing 3a of the lower part 3. By means of rotation about a rotational axis x, which rotation is shown by the direction of the arrow, the optical sensor 4 is movable toward an opening 2 in the lower part 1. Seals 7, for example one or more O-rings, prevent, firstly, the leakage of the medium from the container and, secondly, contamination of the medium by, for example, airborne germs.

According to FIGS. 1a to 2b, the upper part 1 has a base 1a with the opening 2, an cylindrical outer wall 1b projecting from the base 1a and a flange 1c projecting in from an end of the outer wall 1b remote from the base 1a. A spring 6 is mounted on the sensor protector between a step 3b of the sensor housing 3a and the flange 1c and urges the lower part 3 toward the base 1a of the upper part 1. FIG. 1a shows a diagrammatic cross section through an exemplary embodiment of the sensor protector in the closed state, wherein a spring 6 presses the lower part 3 and hence, too, the projection 5 along with the optical sensor 4 onto the upper part 1. Thus, for example, unintended opening during the sterilization is avoidable. FIG. 1b is a top view of an exemplary embodiment of the sensor protector according to FIG. 1a. Here, the mirror-symmetrical position of opening 2 and optical sensor 4 or projection 5 is identifiable. An embodiment with a plurality of openings and projections or optical sensors is also possible.

FIG. 2a shows a diagrammatic cross section through an exemplary embodiment of the sensor protector in the open state. The projection 5, which is smaller than the opening 2, is pushed outward i.e. into the interior of the container by the spring 6. FIG. 2b shows a top view of an exemplary embodiment of the sensor protector according to FIG. 2a.

Figure 4:
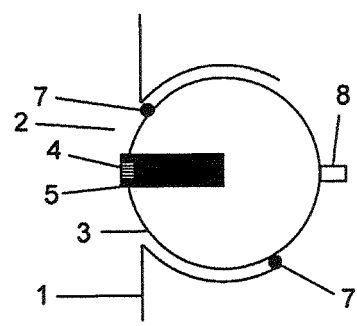
FIG. 4 shows a diagrammatic cross section through an exemplary embodiment of the sensor protector in the open state.

According to FIGS. 3 and 4, the upper part 1 and the lower part 3 form a rotary joint, which is also implementable as a ball joint. The upper part 1 acts as a joint socket. The lower part 3 acts as a joint head and contains the at least one optical sensor 4, which sits in or on a projection 5. A shaft 8 facilitates the opening and closing of the sensor protector. Seals 7 ensure opening and closing without breaking the sterile barrier of the container. FIG. 3 shows a diagrammatic cross section through an exemplary embodiment of the sensor protector in the closed state. Rotation of the lower part 3 in the direction of the arrow opens the sensor protector. FIG. 4 shows a diagrammatic cross section through an exemplary embodiment of the sensor protector in the open state.

The invention claimed is:

1. A sensor protector, comprising: an upper part (1) with a base comprising at least one opening (2) and an outer wall projecting from the base and having an inner surface; and a lower part (3) comprising a sensor housing mounted inward of the inner surface of the outer wall and being dimensioned to permit rotation of the sensor housing about a rotational axis relative to the outer wall and at least one optical sensor (4) mounted in the sensor housing and displaced from the rotational axis, wherein the optical sensor (4), in a first rotational position of the sensor housing, is offset rotationally from the opening (2) of the upper part (1) and, in a second rotational position of the sensor housing, is aligned with the opening (2) of the upper part (1).

2. The sensor protector of claim 1, wherein the lower part (3) comprises at least one projection (5) which comprises the at least one optical sensor (4).

3. The sensor protector of claim 2, wherein the projection (5) is smaller than the opening (2).

4. The sensor protector of claim 1, wherein a surface of the lower part (3) is flush with a surface of the optical sensor (4).

5. The sensor protector of claim 1, wherein a variable force pushes the lower part (3) onto the upper part (1).

6. The sensor protector of claim 5, wherein the variable force is a spring force exerted by a spring (6).

7. The sensor protector according to claim 5, wherein the variable force is a force exerted by a pneumatic or hydraulic system.

8. The sensor protector of claim 1, wherein the upper part (1) and the lower part (3) are made from plastic.

9. The sensor protector of claim 1, wherein the optical sensor (4) is offset sufficiently from the opening (2) of the upper part (1) to permit sterilization by radiation while maintaining the functionality of the optical sensor (4).

10. The sensor protector of claim 9, wherein the radiation is ionizing, gamma or electron radiation.

11. The sensor protector of claim 1, wherein the optical sensor (4) and the opening (2) are at mirror symmetrical positions on opposite respective sides of the rotational axis.

12. The sensor protector of claim 11, wherein the inner surface of the outer wall of the upper part (1) defines at least one cylindrically generated surface concentric with the rotational axis.

13. The sensor protector of claim 12, wherein the base of the upper part (1) is substantially perpendicular to the rotational axis.

14. The sensor protector of claim 13, wherein the upper part (1) further comprises a flange projecting in from the outer wall, the sensor housing further comprising a step between the flange and the base of the upper part (1), the sensor protector further comprising a spring (6) between the flange and the step, the spring being configured for urging the lower part ((3) toward the base of the upper part (1).

15. The sensor protector of claim 12, wherein the base of the upper part (1) is substantially parallel to the rotational axis.

16. The sensor protector of claim 15, further comprising a shaft projecting from a side of the sensor housing opposite the optical sensor (4) and through an opening in the outer wall of the upper part (1) to facilitate rotation of the lower part (3) relative to the upper part (1).

* * * * *